United States Patent
Ruiz Altaba et al.

(10) Patent No.: US 9,351,988 B2
(45) Date of Patent: May 31, 2016

(54) MACROCYCLIC LACTONES AND USE THEREOF

(75) Inventors: Ariel Ruiz Altaba, Geneva (CH); Christophe Mas, Gaillard (FR)

(73) Assignee: UNIVERSITE DE GENEVE, Geneva (CH)

(*) Notice: Subject to any disclaimer, the term of this patent is extended or adjusted under 35 U.S.C. 154(b) by 0 days.

(21) Appl. No.: 14/115,410

(22) PCT Filed: May 1, 2012

(86) PCT No.: PCT/IB2012/052165
§ 371 (c)(1),
(2), (4) Date: Nov. 4, 2013

(87) PCT Pub. No.: WO2012/150543
PCT Pub. Date: Nov. 8, 2012

(65) Prior Publication Data
US 2014/0080779 A1    Mar. 20, 2014

Related U.S. Application Data

(60) Provisional application No. 61/481,348, filed on May 2, 2011.

(51) Int. Cl.
*A61K 31/7048* (2006.01)
*A61K 31/365* (2006.01)
*A61K 45/06* (2006.01)

(52) U.S. Cl.
CPC ............ *A61K 31/7048* (2013.01); *A61K 31/365* (2013.01); *A61K 45/06* (2013.01)

(58) Field of Classification Search
USPC .................................................. 514/30, 450
See application file for complete search history.

(56) References Cited

U.S. PATENT DOCUMENTS

| | | | |
|---|---|---|---|
| 4,144,352 A | 3/1979 | Putter | |
| 4,160,084 A | 7/1979 | Miller et al. | |
| 4,199,569 A | 4/1980 | Chabala et al. | |
| 5,252,474 A | 10/1993 | Gewain et al. | |
| 2009/0281175 A1 | 11/2009 | Kaoukhov et al. | |

FOREIGN PATENT DOCUMENTS

| | | |
|---|---|---|
| WO | WO 2008/034202 | 3/2008 |
| WO | WO 2011/011632 | 1/2011 |

OTHER PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Barker, N. et al. "Mining the Wnt pathway for cancer therapeutics", *Nature Reviews Drug Discovery*, Dec. 2006, pp. 997-1014, vol. 5.
Albers-Schonberg, G. etal. "Avermectins. Structure Determination" *Journal of the American Chemical Society*, 1981, pp. 4216-4221, vol. 103, No. 14.
Burg, R. W. et al. "Avermectins, New Family of Potent Anthelmintic Agents: Producing Organism and Fermentation" *Antimicrobial Agents and Chemotherapy*, Mar. 1979, pp. 361-367, vol. 15, No. 3.
Sharmeen, S. et al. "The anti-parasitic agent ivermectin induces chloride-dependent membrane hyperpolarization and cell death in leukemia cells" *Blood*, Nov. 4, 2010, pp. 3593-3603, vol. 116, No. 18.
Okazaki, T. et al. "Milbemycins, A New Family of Macrolide Antibiotics: Producing Organism and Its Mutants" *The Journal of Antibiotics*, Apr. 1983, pp. 438-441, vol. 36, No. 4.
Danishefsky, S. J. et al. "The Total Synthesis of Avermectin $A_{1a}$." *J. Am. Chem. Soc.*, 1989, pp. 2967-2980, vol. 111, No. 8.
Takiguchi, Y. et al. "Milbemycins*, A New Family of Macrolide Antibiotics: Fermentation, Isolation and Physico-Chemical Properties" *The Journal of Antibiotics*, Oct. 1980, pp. 1120-1127, vol. 33, No. 10.
Takiguchi, Y. et al. "Milbemycins*, A New Family of Macrolide Antibiotics: Fermentation, Isolation and Physico-Chemical Properties of Milbemycins D, E, F, G and H" *The Journal of Antibiotics*, May 1983, pp. 502-508, vol. 36, No. 5.
Pitterna, T. et al. "New ventures in the chemistry of avermectins" *Bioorganic & Medicinal Chemistry*, 2009, pp. 4085-4095, vol. 17.
Davies, H. G. et al. "Avermectins and Milbemycins" *Natural Product Reports*, 1986, pp. 87-121.
Clement, V. et al. "HEDGEHOG-GLI1 Signaling Regulates Human Glioma Growth, Cancer Stem Cell Self-Renewal, and Tumorigenicity" *Current Biology*, Jan. 23, 2007, pp. 165-172, vol. 17.
Reedijk, M. et al. "Activation of Notch signaling in human colon adenocarcinoma" *International Journal of Oncology*, 2008, pp. 1223-1229, vol. 33.
Arteaga, C. L. "Activation of TGFβ signaling in cancer therapy" *Current Opinion in Genetics & Development*, 2006, pp. 30-37, vol. 16.
Luo, J. et al. "Wnt signaling and human diseases: what are the therapeutic implications?" *Laboratory Investigation*, Feb. 2007, pp. 97-103, vol. 87.
Varnat, F. et al. "Human colon cancer epithelial cells harbour active HEDGEHOG-GLI signalling that is essential for tumour growth, recurrence, metastasis and stem cell survival and expansion" *EMBO Molecular Medicine*, 2009, pp. 338-351, vol. 1.

(Continued)

*Primary Examiner* — Kristin Vajda
(74) *Attorney, Agent, or Firm* — Saliwanchik, Lloyd & Eisenschenk (57) ABSTRACT

The present invention is directed to the use of macrocyclic lactones, in particular avermectins, in the treatment of conditions whose formation, occurrence, development or growth is associated with aberrant Wnt signalling, in particular the treatment of colorectal cancer.

20 Claims, 4 Drawing Sheets

(56) References Cited

OTHER PUBLICATIONS

Varnat, F. et al. "Loss of WNT-TCF addiction and enhancement of HH-GLI1 signalling define the metastatic transition of human colon carcinomas" *EMBO Molecular Medicine*, 2010, pp. 440-457, vol. 2, No. 11.

Written Opinion in International Application No. PCT/IB2012/052165, Aug. 30, 2012, pp. 1-16.

Lankas, G. R. et al. "Chapter 6 Toxicology" In Ivermectin and Abamectin, Campbell, W C., *Éd. Springer Verlag*, New York, NY, 1989, pp. 89-112.

Mishima, H. et al. "Structures of Milbemycin $\beta1$, $\beta2$ and $\beta3$" *Tetrahedron Letters*, 1975, pp. 711-714, No. 10.

Mishima, H. et al. "Milbemycins, A New Family of Macrolide Antibiotics Structure Determination of Milbemycins D, E, F, G, H, J and K" *The Journal of Antibiotics*, Aug. 1983, pp. 980-990, vol. 36, No. 8.

Petrelli, N. J. et al. "Combination chemotherapy of cisplatin and 5-fluorouracil for advanced colorectal adenocarcinoma" *Cancer Chemotherapy and Pharmacology*, 1989, pp. 57-60, vol. 23.

Polakis, P. "Wnt signaling and cancer" *Genes & Development*, Aug. 1, 2000, pp. 1837-1851, vol. 14, No. 15.

Huang, S.-M.A., et al., "Tankyrase inhibition stabilizes axin and antagonizes Wnt signaling," *Nature*, Oct. 2009, vol. 461, pp. 614-620.

Kikuchi, A., et al., "Wnt5a: its signalling, functions and implication in diseases," *Acta Physiologica*, 2012, vol. 204, pp. 17-33.

Monroe, D.G., et al., "Update on Wnt signaling in bone cell biology and bone disease," *Gene*, 2012, vol. 492, pp. 1-18.

Westendorf, J.J., et al., "Wnt signaling in osteoblasts and bone diseases," *Gene*, 2004, vol. 341, pp. 19-39.

* cited by examiner

| | | Ivermectin µM | | | | | | Abamectin µM | | | | | | Doramectin µM | | | | | | Moxidectin µM | | | | | |
|---|---|---|---|---|---|---|---|---|---|---|---|---|---|---|---|---|---|---|---|---|---|---|---|---|---|
| | | 0.5 | 1 | 2.5 | 5 | 10 | IC$_{50}$ | 0.5 | 1 | 2.5 | 5 | 10 | IC$_{50}$ | 0.5 | 1 | 2.5 | 5 | 10 | IC$_{50}$ | 0.5 | 1 | 2.5 | 5 | 10 | IC$_{50}$ |
| Colon cancer | LS174T | n.d | 95 | 31 | 14 | 6 | 1.9 | 73 | 55 | 30 | 0 | 0 | 1.2 | 86 | 41 | 17 | 0 | 0 | 0.9 | 98 | 85 | 72 | 45 | 12 | 4.5 |
| | CC14* | n.d | 68 | 57 | 6 | 0 | 2.4 | 70 | 40 | 32 | 0 | 0 | 0.8 | n.d | n.d | n.d | n.d | n.d | n.d | n.d | n.d | n.d | n.d | n.d | n.d |
| | CC36* | n.d | 53 | 14 | 0 | 0 | 1.1 | 75 | 55 | 42 | 10 | 0 | 1.4 | n.d | n.d | n.d | n.d | n.d | n.d | n.d | n.d | n.d | n.d | n.d | n.d |
| Gliobastoma | BT57* | 116 | 100 | 16 | 0 | 0 | 1.7 | 100 | 114 | 48 | 0 | 0 | 2.5 | 98 | 96 | 0 | 0 | 0 | 1.2 | n.d | n.d | n.d | n.d | n.d | n.d |

*primary tumor
n.d: "not determined"

MACROCYCLIC LACTONES AND USE THEREOF

CROSS-REFERENCE TO RELATED APPLICATIONS

This application is the U.S. national stage application of International Patent Application No. PCT/IB2012/052165, filed May 1, 2012, which claims the benefit of U.S. Provisional Patent Application No. 61/481,348, filed May 2, 2011.

FIELD OF THE INVENTION

The present invention is related to the use of macrocyclic lactones in colorectal cancer treatment.

BACKGROUND OF THE INVENTION

Colorectal cancer (CRC) is the third most common tumor type and a leading cause of cancer death in both men and women. Despite improved prognosis for colorectal cancer patients in the last decade, it still causes considerable morbidity and mortality and survival rates lag behind those of breast and prostate cancer patients.

Causes of CRC are believed to be a result of interactions between inherited and environmental factors. The primary risk factor of CRC is age as 90% of the cases are diagnosed over the age of 50 years. Other reported risks include, among others, familial history of adenomatous polyposis, people suffering from inflammatory bowel disease (IBD), Crohn's disease, ulcerative colitis, diabetes, physical inactivity, obesity, smoking, high alcohol intake and a diet rich in animal fat.

In most cases, CRCs develop slowly over a period of several years. Symptoms of colon cancer do not appear in all patients when the disease is in an early stage but only after it has advanced in gravity. Most CRCs begin as a polyp, a growth of tissue that starts in the lining and grows into the center of the colon or rectum. There are several types of polyps: adenomas, which can become cancerous but are easily removed during a colonoscopy; inflammatory polyps which appear after ulcerative colitis and can also become cancerous and hyperplastic polyps which rarely transform into cancer. 95% of colorectal cancers are adenocarcinomas.

Colorectal cancer has distinct stages and the most commonly used staging system for colorectal cancer is that of the American Joint Committee on Cancer (AJCC), sometimes also known as the TNM system. Older staging systems for colorectal cancer include the Dukes and Astler-Coller systems. The stage describes to what extent the cancer has spread in the body: how far the cancer has grown into the wall of the intestine (primary tumor status, "T"), whether or not it has spread to the lymph nodes (nodal status, "N"), and whether or not it has reached nearby structures (metastatic status, "M"). According to TNM status, patients are assigned one of four stages: I, II, III or IV. The stage of a cancer is one of the most important factors in determining prognosis and treatment options. Each stage has different treatment options. Treatment of cancer is curative when diagnosed at early stage but prognosis is poorer at later stages.

Surgery is the preferred treatment approach for early-stage colorectal cancer, allowing patients to make a full recovery. Standard regimens in the first and second-line treatment settings are selected from "XELOX" (Capecitabine and oxaliplatin), "FOLFIRI" (5-fluorouracil, leucovirin and irinotecan) and "FOLFOX" (5-fluorouracil, leucovirin and oxaliplatin). However, while adjuvant chemotherapy (a combination of fluoropyrimidines such as capecitabine with oxaliplatin or irinotecan) has been shown to extend survival in stage IIb (advanced and metastatic stage), clinical benefit in early stages of the disease remains unclear. The emergence of antibody therapies such as AVASTIN (bevacizumab, Genentech/Roche/Chugai), ERBITUX (cetuximab, Eli Lilly/Merck KGaA/Bristol-Myers Squibb) and VECTIBIX (panitumumab, Amgen), respectively targeting the vascular endothelial growth factor (VEGF) or the epidermal growth factor (EGFR) for colorectal cancer management, has helped to improve patient prognosis further.

The Wnt pathway is instrumental in orchestrating proper tissue development in embryos and normal tissue maintenance in adults. This is achieved by directing a specific set of genes that are responsible for the control of cell growth, movement and survival. It has been found that chronic activation of the Wnt pathway in intestinal epithelial cells drives their expansion into benign adenomas (also known as polyps), which frequently progress to invasive colon carcinoma following additional genetic mutations facilitating their progression into malignant, invasive and metastatic cancers (Barker and Clevers, 2006, *Nature Reviews Drug Discovery*, 5, 997-1014; Polakis, 2000, *GenesDev*, 14, 1837-1851). A range of other cancers also present signs of aberrant Wnt signaling activity but clear mutations in key Wnt signaling components have been identified with less frequency than in colon cancer. It is believed that abnormal activation of the various genes resulting from aberrant activation of the Wnt pathway may promote uncontrolled cell growth and survival, and consequently may also drive cancer formation and growth in a broad range of tissues, including breast, skin and brain. Aberrant Wnt signaling is also implicated in other conditions such as rheumatoid arthritis, neurological disorders and bone diseases (Barker and Clevers, 2006, supra).

Macrocyclic lactones are fermentation products, or chemical derivatives thereof, of microorganisms such as those belonging to the genus *Streptomyces*, classified in two groups: Avermectins (including ivermectin, abamectin, doramectin, eprinomectin, and selamectin), derived from *Streptomyces avermitilis* and Milbemycins (including milbemycin oxime and moxidectin), derived from *Streptomyces hygroscopicus* or *Streptomyces cyanogriseus*.

The family of Avermectins covers closely related compounds and semi-synthetic mixtures thereof (Albers-Schönberg et al., 1981, *J. Am. Chem. Soc.*, 103, 4216-4221). They have been described as antiparasitic agents, particularly active against nematodes and arthropods. Avermectins have found wide application as pesticides and antiparasitic agents for human and animal use (e.g. cattle, sheep, horses) (Burg et al., 1979, *Antimicrob. Agents Chemother.*, 15, 361-367). Among Avermectins, Abamectin and one of its synthetic derivatives, Ivermectin, are the most extensively used compounds. Abamectin is used to control insect and mite pests in agriculture and fire ants. Abamectin is also used as a veterinary anthelmintic. Ivermectin is used for the treatment of the parasitic infections strongyloidiasis and onchocerciasis (river blindness) in humans and other worm infestations (e.g., ascariasis, trichuriasis and enterobiasis) and is commercialized under the name of MECTIZAN/STROMECTOL (Merck & Co. Inc.) for oral treatment of onchocerciasis caused by *Onchocerca volvulus*. Ivermectin has been recently described as presenting anti-leukemic activity in acute myeloid leukemia (AML) cell lines (Sharmeen et al., 2010, *Blood, Vol.* 116(18), 3593-3603).

The family of Milbemycins exhibit structures that are related to Avermectins' structures (Albers-Schönberg et al., 1981, above; Mishima et al., 1974, *Abstract papers, 18th Symp. Chem. Natural Products,* 309-316, Kyoto, October 17-19; Mishima et al., 1975, *Tetrahydron Lett.,* 711-714; Okazaki et al., 1983, *J. Antibiotics,* 36, 438-441). As Avermectins, the family of Milbemycins covers closely related compounds and semisynthetic mixtures thereof are known to have insecticidal, acaricidal and anthelmintic activities (U.S. Pat. No. 4,144,352).

Despite advances in chemotherapy, the majority of patients with advanced tumors eventually succumb to their disease, and the aging of the population, the increase in the prevalence of risk factors such as obesity and diabetes and increasing sedentary lifestyles contribute to a rise of the overall incidence of colorectal cancer. Therefore, the development of new therapies for colorectal cancer, notably treatments that prevent early-stage colorectal cancer from evolving into advanced and metastatic stages, would be highly desirable.

SUMMARY OF THE INVENTION

The invention relates to the unexpected finding of Wnt signaling pathway inhibitory activity of macrocyclic lactones. The invention further relates to the unexpected finding of the ability of macrocyclic lactones to inhibit proliferation of cell lines, primary and metastatic colon cancer cells in vitro, and human colon cancer xenografts in vivo.

A first aspect of the invention provides macrocyclic lactones as well as tautomers, geometrical isomers, optically active forms, enantiomeric mixtures thereof, pharmaceutically acceptable salts, pharmaceutically active derivatives and mixtures thereof for use in regenerative medicine and/or for the prevention, repression or treatment of a colorectal cancer.

A second aspect of the invention provides a use of macrocyclic lactones as well as tautomers, geometrical isomers, optically active forms, enantiomeric mixtures thereof, pharmaceutically acceptable salts, pharmaceutically active derivatives and mixtures thereof for the preparation of a pharmaceutical composition for the prevention, repression or treatment of a colorectal cancer.

A third aspect of the invention provides a use of macrocyclic lactones as well as tautomers, geometrical isomers, optically active forms, enantiomeric mixtures thereof, pharmaceutically acceptable salts, pharmaceutically active derivatives and mixtures thereof for the preparation of a pharmaceutical composition for use in regenerative medicine.

A fourth aspect of the invention provides macrocyclic lactones as well as tautomers, geometrical isomers, optically active forms, enantiomeric mixtures thereof, pharmaceutically acceptable salts, pharmaceutically active derivatives and mixtures thereof for the modulation of Wnt signalling.

A fifth aspect of the invention provides a use of macrocyclic lactones as well as tautomers, geometrical isomers, optically active forms, enantiomeric mixtures thereof, pharmaceutically acceptable salts, pharmaceutically active derivatives and mixtures thereof for the preparation of a pharmaceutical composition for the modulation of Wnt signalling.

A sixth aspect of the invention provides a method of preventing, repressing or treating a colorectal benign (adenoma) or malignant tumor and cancer in a subject, said method comprising administering to a subject in need thereof a therapeutically effective amount of a macrocyclic lactone, a tautomer, a geometrical isomer, an optically active form, an enantiomeric mixture, a pharmaceutically acceptable salt, a pharmaceutically active derivative thereof or a mixture thereof.

A seventh aspect of the invention provides a method of regenerating a damaged organ or tissue or enhancing the state or function of an organ or tissue of a subject, said method comprising administering to a subject in need thereof an effective amount of macrocyclic lactone or a tautomer, a geometrical isomer, an optically active form, an enantiomeric mixture, a pharmaceutically acceptable salt, a pharmaceutically active derivative or a mixture thereof to induce cell regeneration in said organ or tissue of said patient or adding an effective amount of macrocyclic lactone or a tautomer, a geometrical isomer, an optically active form, an enantiomeric mixture, a pharmaceutically acceptable salt, a pharmaceutically active derivative, or a mixture thereof to an ex-vivo culture of an organ, tissue or cell for subsequent implantation into said patient.

An eighth aspect of the invention provides a method of modulating Wnt signalling in a subject, said method comprising administering to a subject in need thereof an effective amount of macrocyclic lactone or a tautomer, a geometrical isomer, an optically active form, an enantiomeric mixture, a pharmaceutically acceptable salt, a pharmaceutically active derivative thereof or a mixture thereof to induce modulation of Wnt signalling in said patient, in particular, downregulating of the Wnt signalling.

A ninth aspect of the invention provides a pharmaceutical formulation comprising a macrocyclic lactone or a tautomer, a geometrical isomer, an optically active form, an enantiomeric mixture, a pharmaceutically acceptable salt, a pharmaceutically active derivative thereof or a mixture thereof, combined with at least one co-agent useful in the treatment of colorectal cancer, and at least one pharmaceutically acceptable carrier.

A tenth aspect of the invention provides a cell culture composition comprising a macrocyclic lactone or a tautomer, a geometrical isomer, an optically active form, an enantiomeric mixture, a pharmaceutically acceptable salt, a pharmaceutically active derivative thereof or a mixture thereof, combined with at least one co-agent useful in cell regeneration.

An eleventh aspect of the invention provides macrocyclic lactones as well as tautomers, geometrical isomers, optically active forms, enantiomeric mixtures thereof, pharmaceutically acceptable salts, pharmaceutically active derivatives and mixtures thereof for use in the treatment of conditions associated with aberrant Wnt signaling including the treatment of breast cancer, melanoma, head and neck cancer, lung cancer, gastric cancer, mesothelioma, glioblastoma, medulloblastoma and cervical cancer.

DETAILED DESCRIPTION OF THE INVENTION

The term "macrocyclic lactone" as used in the context of the invention covers fermentation products, or chemical derivatives thereof, of microorganisms, in particular soil microorganisms, such as those belonging to the genus *Streptomyces*. In particular, macrocyclic lactones comprise fermentation products, or chemical derivatives thereof, produced for example by *Streptomyces avermitilis*, also called Avermectins and produced for example by *Streptomyces hygroscopicus*, also called Milbemycins. The term "Avermectins" covers compounds that are described in Albers-Schönberg et al., 1981, above; Danishefsky et al., 1989, *J. Am. Chem. Soc.*, 111, 2967-2980; Burg et al., 1979; Lankas et al., 1989, *Toxicology, In Ivermectin and Abamectin*, Campbell, W. C., Ed. Springer Verlag, New York, N.Y., 1989, 10-142; U.S. Pat. No. 4,199,59; and US 2009/0281175) and derivatives or mixtures thereof. In particular, Avermectins comprise ivermectin, abamectin, doramectin, eprinomectin, and selamectin.

The term "Abamectin" covers a mixture of Avermectin B1a and Avermectin B1b. In particular, Abamectin covers a mixture of macrocyclic lactones comprising at least 80% of Avermectin B1a and about or less than 20% of Avermectin B1b. Abamectin comprises a commercial compound commercialized under the names of AFFIRM, AVID (Syngenta) and ZEPHYL.

The term "Avermectin B1a" covers a macrocyclic lactone of Formula (I) wherein —X— is —CH=CH—, —Y— is —CH(OH)—, Z is —CH$_2$CH$_3$, W is a group of Formula (II) wherein R$^1$ is OH and n is 1. In particular, Avermectin B1a is a compound of the following Formula (III):

Formula (III)

also named (10E,14E,16E)-(1R,4S,5'S,6S,6'R,8R,12S,13S,20R,21R,24S)-6'-[(S)-sec-butyl]-21,24-dihydroxy-5',11,13,22-tetramethyl-2-oxo-(3,7,19-trioxatetracyclo [15.6.1.1$^{4,8}$.0$^{20,24}$]pentacosa-10,14,16,22-tetraene)-6-spiro-2'-(5',6'-dihydro-2'H-pyran)-12-yl 2,6-dideoxy-4-O-(2,6-dideoxy-3-O-methyl-α-L-arabino-hexopyranosyl)-3-O-methyl-α-L-arabino-hexopyranoside.

The term "Avermectin B1b" covers a macrocyclic lactone of Formula (I) wherein —X— is —CH=CH—, —Y— is —CH(OH)—, Z is —CH$_3$, W is a group of Formula (II) wherein R$^1$ is OH and n is 1. In particular, Avermectin B1a is a compound of the following Formula (IV):

Formula (IV)

also named (10E,14E,16E)-(1R,4S,5'S,6S,6'R,8R,12S,13S,20R,21R,24S)-21,24-dihydroxy-6'-isopropyl-5',11,13,22-tetramethyl-2-oxo-(3,7,19-trioxatetracyclo[15.6.1.1$^{4,8}$.0$^{20,24}$]pentacosa-10,14,16,22-tetraene)-6-spiro-2'-(5',6'-dihydro-2'H-pyran)-12-yl 2,6-dideoxy-4-O-(2,6-dideoxy-3-O-methyl-α-L-arabino-hexopyranosyl)-3-O-methyl-α-L-arabino-hexopyranoside. The term "Doramectin" covers a macrocyclic lactone of Formula (I) wherein —X— is —CH=CH—, —Y— is —CH(OH)—, Z is cyclohexyl, W is a group of Formula (II) wherein R$^1$ is OH and n is 1. In particular, Avermectin B1a is a compound of the following Formula (V):

Formula (V)

also named 25-cyclohexyl-5-O-demethyl-25-de(1-methylpropyl)avermectin $A_{1a}$ or (10E,14E,16E)-(1R,4S,5'S,6S,6'R,8R,12S,13S,20R,21R,24S)-6'-cyclohexyl-21,24-dihydroxy-5',11,13,22-tetramethyl-2-oxo-(3,7,19-trioxatetracyclo[15.6.1.1$^{4,8}$.0$^{20,24}$]pentacosa-10,14,16,22-tetraene)-6-spiro-2'-(5',6'-dihydro-2'H-pyran)-12-yl2,6-dideoxy-4-O-(2,6-dideoxy-3-O-methyl-α-L-arabino-hexopyranosyl)-3-O-methyl-α-L-arabino-hexopyranoside. Doramectin comprises a commercial compound commercialized under the name of DECTOMAX (Pfizer).

The term "Ivermectin" covers a mixture of 22,23-Dihydroxy-Avermectin B1a and 22,23-Dihydroxy-Avermectin B1b. In particular, Ivermectin covers a mixture of macrocyclic lactones comprising at least 90% of 22,23-Dihydroxy-Avermectin B1a and about or less than 10% of 22,23-Dihydroxy-Avermectin B1b. 22,23-Dihydroxy-Avermectin B1a is also named (10E,14E,16E)-(1R,4S,5'S,6R,6'R,8R,12S,13S,20R,21R,24S)-6'-[(S)-sec-butyl]-21,24-dihydroxy-5',11,13,22-tetramethyl-2-oxo-(3,7,19-trioxatetracyclo[15.6.1.1$^{4,}$ $_8$.0$^{20,24}$]pentacosa-10,14,16,22-tetraene)-6-spiro-2'-(tetrahydro pyran)-12-yl 2,6-dideoxy-4-O-(2,6-dideoxy-3-O-methyl-α-L-arabino-hexopyranosyl)-3-O-methyl-α-L-arabino-hexopyranoside. 22,23-Dihydroxy-Avermectin B1b is also named (10E,14E,16E)-(1R,4S,5'S,6R,6'R,8R,12S,13S,20R,21R,24S)-21,24-dihydroxy-6'-isopropyl-5',11,13,22-tetramethyl-2-oxo-(3,7,19-trioxatetracyclo[15.6.1.1$^{4,}$ $_8$.0$^{20,24}$]pentacosa-10,14,16,22-tetraene)-6-spiro-2'-(tetrahydro pyran)-12-yl 2,6-dideoxy-4-O-(2,6-dideoxy-3-O-methyl-α-L-arabino-hexopyranosyl)-3-O-methyl-α-L-arabino-hexo pyranoside. Ivermectin comprises a commercial compound commercialized under the names of STROMECTOL (Merck & Co., Inc.) or MECTIZAN.

The term "Milbemycins" covers compounds are described in Takigushi et al., 1980, *J. Antibiotics*, 33, 1120-1127; Mishima et al., 1974, above; Mishima et al., 1975, above; Okazaki et al., 1983, above; Takigushi et al., 1983, *The Journal of Antibiotics*, XXXVI (5), 502-508; and U.S. Pat. No. 4,144,352 and derivatives or mixtures thereof. In particular, Milbemycins comprise milbemectin, milbemycin B or moxidectin, milbemycin D, Nemadectin and milbemycin oxime.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it, such as a preventive early asymptomatic intervention; (b) inhibiting the disease, i.e., arresting its development; or (c) relieving the disease, i.e., causing regression of the disease and/or its symptoms or conditions, such as improvement or remediation of damage. In particular, the methods, uses, formulations and compositions according to the invention are useful in the treatment of colorectal cancer and/or in the prevention of evolution of a colorectal cancer into an advanced or metastatic stage in patients with early stage colorectal cancer, thereby improving the cancer staging and patient prognosis.

The methods, uses, formulations and compositions according to the invention are also useful in the treatment of conditions associated with aberrant Wnt signaling including the treatment of breast cancer, melanoma, head and neck cancer, lung cancer, gastric cancer, mesothelioma, glioblastoma, medulloblastoma and cervical cancer, and/or in the prevention of evolution of those cancer conditions into an advanced or metastatic stage in patients with early stage cancer conditions.

The term "subject" as used herein refers to mammals. For examples, mammals contemplated by the present invention include humans, primates, domesticated animals such as cattle, sheep, pigs, and horses, laboratory rodents, other pets and the like.

The term "effective amount" as used herein refers to an amount of at least one polypeptide or a pharmaceutical formulation thereof according to the invention that elicits the biological or medicinal response in a tissue, system, animal or human that is being sought. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term as used herein also includes the amount of active polypeptide sufficient to reduce the progression of the disease, notably to reduce or inhibit the tumor growth and thereby elicit the response being sought (i.e. an "inhibition effective amount").

The term "efficacy" of a treatment according to the invention can be measured based on changes in the course of a disease in response to a use or a method according to the invention. For example, the efficacy of a treatment of a colorectal cancer can be measured by monitoring the number or size of tumors detected during colonoscopy or by imaging, and by the serial measurement of appropriate blood tumor-specific markers (such as carcinoembryonic antigen (CEA)). Effective treatment is indicated by reduction in tumor number or size, and diminishing levels or maintenance of basal levels of at least one tumor-specific marker. A successful outcome results in an increase of progression-free survival time, and/or a decreased risk of relapse post-resection for primary colorectal cancer. For example, the efficacy of a treatment in regenerative medicine can be measured by monitoring the cell regeneration, such as nerve cell regeneration.

The following paragraphs provide definitions of the various chemical moieties that make up the compounds according to the invention and are intended to apply uniformly throughout the specification and claims, unless an otherwise expressly set out definition provides a broader definition.

The term "$C_1$-$C_6$ alkyl" when used alone or in combination with other terms comprises a straight chain or branched $C_1$-$C_6$ alkyl which refers to monovalent alkyl groups having 1 to 6 carbon atoms.

The term "$C_2$-$C_6$ alkenyl" when used alone or in combination with other terms comprises a straight chain or branched $C_2$-$C_6$ alkenyl. It may have any available number of double bonds in any available positions, and the configuration of the double bond may be the (E) or (Z) configuration.

The term "$C_3$-$C_8$-cycloalkyl" refers to a saturated carbocyclic group of from 3 to 8 carbon atoms having a single ring (e.g., cyclohexyl) or multiple condensed rings.

Unless otherwise constrained by the definition of the individual substituent, all the above substituents should be understood as being all optionally substituted.

Unless otherwise constrained by the definition of the individual substituent, the term "substituted" refers to groups substituted with from 1 to 5 substituents selected from the group consisting of "$C_1$-$C_6$ alkyl," "$C_2$-$C_6$ alkenyl," "$C_2$-$C_6$ alkynyl," "$C_3$-$C_8$-cycloalkyl," "heterocycloalkyl," "$C_1$-$C_6$ alkyl aryl," "$C_1$-$C_6$ alkyl heteroaryl," "$C_1$-$C_6$ alkyl cycloalkyl," "$C_1$-$C_6$ alkyl heterocycloalkyl," "amino," "aminosulfonyl," "ammonium," "acyl amino," "amino carbonyl," "aryl," "heteroaryl," "sulfinyl," "sulfonyl," "alkoxy," "alkoxy carbonyl," "carbamate," "sulfanyl," "halogen," trihalomethyl, cyano, hydroxy, mercapto, nitro, and the like.

The term "regenerative medicine" is defined as the regeneration of damaged organs or tissues in situ via the therapeutic stimulation of cell regeneration in a patient, or by the growth of replacement tissue in the laboratory or in donor animals for subsequent implantation into a patient. Regenerative medicine aims to treat currently incurable disorders, including neurodegenerative diseases such as Parkinson's disease, muscular dystrophy and multiple sclerosis, and to repair or replace nerve cells damaged by spinal cord injury.

"Pharmaceutically active derivative" refers to any compound that upon administration to the recipient is capable of providing, directly or indirectly, the activity disclosed herein. The term "indirectly" also encompasses prodrugs which may be converted to the active form of the drug via endogenous enzymes or metabolism. The prodrug is a derivative of the compound according to the invention and presents tumor growth inhibiting activity that has a chemically or metabolically decomposable group, and a compound that may be converted into a pharmaceutically active compound in vivo under physiological conditions.

The term "pharmaceutical formulation" refers to preparations which are in such a form as to permit biological activity of the active ingredient(s) to be unequivocally effective and which contain no additional component which would be toxic to subjects to which the said formulation would be administered.

Macrocyclic Lactones According to the Invention

According to one aspect, a macrocyclic lactone according to the invention encompasses a macrocyclic lactone as described herein, as well as tautomers, geometrical isomers, optically active forms, enantiomeric mixtures thereof, pharmaceutically acceptable salts and pharmaceutically active derivatives thereof.

According to one particular embodiment, a macrocyclic lactone according to the invention is a macrocyclic lactone of Formula (I):

Formula (I)

as well as tautomers, geometrical isomers, optically active forms, enantiomeric mixtures thereof, pharmaceutically acceptable salts and pharmaceutically active derivatives thereof, wherein —X— is selected from —CH=CH—, —CH$_2$—CH(OH)—, —(CH$_2$)$_2$— and —CH$_2$—C(=N—OCH$_3$)—, —Y— is selected from —CH(OH)—, —C(=N—OH)— and —CH(OCH$_3$)—, Z is selected from optionally substituted $C_1$-$C_6$ alkyl such as optionally substituted propyl (e.g. isopropyl, methyl-1 propyl), optionally substituted $C_2$-$C_6$ alkenyl such as optionally substituted hexenyl (e.g. —C(CH$_3$)=CH—CH(CH$_3$)$_2$) and optionally substituted $C_3$-$C_8$-cycloalkyl such as optionally substituted cyclohexyl (e.g. cyclohexyl), and W is selected from H and a group of Formula (II):

Formula (II)

wherein $R^1$ is selected from —OH, —NH—C(O)—CH$_3$ and —NH—CH$_3$ and n is an integer selected from 0 and 1.

According to another further embodiment, macrocyclic lactones are macrocyclic lactones of Formula (I) as well as tautomers, geometrical isomers, optically active forms, enantiomeric mixtures thereof, pharmaceutically acceptable salts and pharmaceutically active derivatives thereof, wherein —X— is —CH=CH—, —Y— is —CH(OH)—, —Z— is optionally substituted alkyl, and W is a group of Formula (II) wherein $R^1$ is OH and n is 1.

According to another further embodiment, macrocyclic lactones are macrocyclic lactones of Formula (I) as well as tautomers, geometrical isomers, optically active forms, enantiomeric mixtures thereof, pharmaceutically acceptable salts and pharmaceutically active derivatives thereof, wherein —X— is —CH=CH—, —Y— is —CH(OH)—, —Z— is optionally substituted $C_3$-$C_8$-cycloalkyl, and W is a group of Formula (II) wherein $R^1$ is OH and n is 1.

According to another further embodiment, macrocyclic lactones are macrocyclic lactones of Formula (I) as well as tautomers, geometrical isomers, optically active forms, enantiomeric mixtures thereof, pharmaceutically acceptable salts and pharmaceutically active derivatives thereof, wherein —X— is —CH$_2$—CH$_2$—, —Y— is —CH(OH)—, —Z— is optionally substituted alkyl, and W is a group of Formula (II) wherein R$^1$ is OH and n is 1.

According to another further embodiment, macrocyclic lactones are macrocyclic lactones of Formula (I) as well as tautomers, geometrical isomers, optically active forms, enantiomeric mixtures thereof, pharmaceutically acceptable salts and pharmaceutically active derivatives thereof, wherein W is H and X, Y, Z, R$^1$ and n are as described above.

According to another further embodiment, macrocyclic lactones are Avermectins. Avermectins can be isolated by standard methods known to the skilled person, for example as described in U.S. Pat. No. 4,160,084 and Albers-Schönberg et al., 1981, above, or by genetic engineering of microorganisms as described in U.S. Pat. No. 5,252,474 or by synthetic methods described in Danishefsky et al., 1989, above and in Pitterna 2009, *Bioorganic & Medicinal Chemistry* 17, 4085-4095.

According to another further embodiment, a macrocyclic lactone according to the invention is Abamectin.

According to another further embodiment, a macrocyclic lactone according to the invention is Avermectin B1a.

According to another further embodiment, a macrocyclic lactone according to the invention is Avermectin B1b.

According to another further embodiment, a macrocyclic lactone according to the invention is Doramectin.

According to another further embodiment, a macrocyclic lactone according to the invention is Ivermectin.

According to another further embodiment, a macrocyclic lactone according to the invention is Moxidectin.

In another further embodiment, macrocyclic lactones are Milbemycins. Milbemycins can be isolated by standard methods known to the skilled person, for example as described in Takigushi et al., 1983, above or by synthetic methods described in Davies et al., 1986, *Nat. Prod. Rep.*, 87.

According to another embodiment, a macrocyclic lactone or a mixture of macrocyclic lactones is provided for use in regenerative medicine, in particular for the treatment of neurodegenerative diseases such as Parkinson's disease, multiple sclerosis or neuromuscular degenerative disorders such as muscular dystrophy or spinal cord injuries.

According to another embodiment, a macrocyclic lactone or a mixture of macrocyclic lactones is provided for the prevention and/or treatment of colorectal cancer.

According to another embodiment, a macrocyclic lactone or a mixture of macrocyclic lactones is provided for the modulation of Wnt signalling, in particular for the treatment of a disorder selected from a neurodegenerative disorder, a bone disorder, a cardiovascular disorder and a metabolic disorder.

According to another embodiment, a macrocyclic lactone or a mixture of macrocyclic lactones is provided for the modulation of Wnt signalling, in particular for the treatment of a disorder or condition associated with aberrant Wnt signaling, such as a disorder or condition selected from breast cancer, melanoma, head and neck cancer, lung cancer, gastric cancer, mesothelioma, glioblastoma, medulloblastoma and cervical cancer.

According to another embodiment, a macrocyclic lactone or a mixture of macrocyclic lactones is provided for the treatment of a disorder selected from a neurodegenerative disorder, a bone disorder, a cardiovascular disorder and a metabolic disorder.

According to another embodiment, a use of a macrocyclic lactone or a mixture of macrocyclic lactones is provided for the manufacture of a pharmaceutical preparation for the prevention and/or treatment of colorectal cancer.

According to another embodiment, a use of a macrocyclic lactone or a mixture of macrocyclic lactones is provided for the manufacture of a pharmaceutical preparation for use in regenerative medicine.

According to another embodiment, a use of a macrocyclic lactone or a mixture of macrocyclic lactones is provided for the manufacture of a pharmaceutical preparation for the modulation of Wnt signalling, in particular for the treatment of a disorder selected from a neurodegenerative disorder, a bone disorder, a cardiovascular disorder and a metabolic disorder.

According to another embodiment, a use of a macrocyclic lactone or a mixture of macrocyclic lactones is provided for the manufacture of a pharmaceutical preparation for the treatment of the modulation of Wnt signalling, in particular for the treatment of a disorder or condition associated with aberrant Wnt signaling, such as a disorder or condition selected from breast cancer, melanoma, head and neck cancer, lung cancer, gastric cancer, mesothelioma, glioblastoma, medulloblastoma and cervical cancer.

Compositions According to the Invention

The invention provides pharmaceutical or therapeutic agents as compositions and methods for treating a subject, preferably a mammalian subject, and most preferably a human patient who is suffering from a medical disorder, and in particular a disorder mediated by Wnt signalling, in particular colorectal cancer.

The invention further provides pharmaceutical or therapeutic agents as compositions and methods for treating a subject, preferably a mammalian subject, and most preferably a human patient who is suffering from melanoma or glioblastoma.

Compositions or formulations according to the invention may be administered as a pharmaceutical formulation which can contain one or more macrocyclic lactones according to the invention in any form described herein.

The compositions according to the invention, together with a conventionally employed adjuvant, carrier, diluent or excipient, may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use by injection or continuous infusion. Injectable compositions are typically based on injectable sterile saline or phosphate-buffered saline or other injectable carriers known in the art. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Compositions of the invention may be liquid formulations including, but not limited to, aqueous or oily suspensions, solutions, emulsions, syrups, and elixirs. The compositions may also be formulated as a dry product for reconstitution with water or other suitable vehicle before use. Such liquid preparations may contain additives including, but not limited to, suspending agents, emulsifying agents, non-aqueous vehicles and preservatives. Suspending agents include, but are not limited to, sorbitol syrup, methyl cellulose, glucose/sugar syrup, gelatin, hydroxyethyl cellulose, carboxymethyl cellulose, aluminum stearate gel, and hydrogenated edible fats. Emulsifying agents include, but are not limited to, lecithin, sorbitan monooleate, and acacia. Preservatives include, but are not limited to, methyl or propyl p-hydroxybenzoate and sorbic acid. Dispersing or wetting agents include but are not limited to poly(ethylene glycol), glycerol, bovine serum albumin, TWEEN, and SPAN.

Compositions of this invention may also be formulated as a depot preparation, which may be administered by implantation or by intramuscular injection.

Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, acacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

The compounds of the invention can also be administered in sustained release forms or from sustained release drug delivery systems.

According to a particular embodiment, compositions according to the invention are for oral use.

In another particular aspect, the compositions according to the invention are adapted for delivery by repeated administration.

In another particular aspect, the compositions according to the invention are adapted for cell culture for use in regenerative medicine.

Further materials as well as formulation processing techniques and the like are set out in *Part 5 of Remington's Pharmaceutical Sciences, 21st Edition,* 2005, University of the Sciences in Philadelphia, Lippincott Williams & Wilkins, which is incorporated herein by reference.

Mode of Administration

Compounds and formulations thereof according to the invention may be administered in any manner including orally, parenterally, intravenously, rectally, or combinations thereof. Parenteral administration includes, but is not limited to, intravenous, intra-arterial, intra-peritoneal, subcutaneous and intramuscular. The compositions of the invention may also be administered in the form of an implant, which allows slow release of the compositions as well as a slow controlled i.v. infusion.

Combination

According to the invention, the macrocyclic lactones and pharmaceutical formulations thereof can be administered alone or in combination with a co-agent useful for treating, and/or stabilizing, colorectal cancer and/or preventing colorectal cancer from relapsing, such as substances used in conventional chemotherapy and radiation therapy directed against solid tumors and for control of establishment of metastases or any other molecule that acts by triggering programmed cell death, differentiation or permanent senescence, e.g. a co-agent selected from an agent that modulates the hedgehog (Hh)-GLI signaling pathway such as cyclopamine (Clement et al., 2007, *Current Biol.* 17, 165-172), an antimitotic agent such as Cisplatin (Petrelli et al., 1989, *Cancer Chemother. Pharmacol.,* 23, 57-6), an alkylating agent such as Temozolomide (Clement et al., 2007, *Current Biol.,* 17, 165-172) and anti-Notch (Reedijk et al., 2008, *Int. J. Oncol.,* 33, 1223-9) or anti-TGFβ molecules (Arteaga et al., 2006, *Current Opinion in Genetics & Development,* 16:30-37).

The invention encompasses the administration of a macrocyclic lactone or a formulation thereof according to the invention wherein it is administered to a subject prior to, simultaneously or sequentially with other therapeutic regimens or co-agents useful for treating, and/or stabilizing, colorectal cancer and/or preventing colorectal cancer from relapsing. According to the invention, the macrocyclic lactones, and pharmaceutical formulations thereof can be administered alone or in combination with a co-agent useful for inducing cell regeneration, in particular nerve regeneration (e.g. multiple drug regimens), in a therapeutically effective amount.

A macrocyclic lactone or a formulation thereof according to the invention that is administered simultaneously with said co-agents can be administered in the same or different composition(s) and by the same or different route(s) of administration.

According to one embodiment, a pharmaceutical formulation is provided comprising a macrocyclic lactone, combined with at least one co-agent useful for treating, and/or stabilizing, colorectal cancer and/or preventing colorectal cancer from relapsing, and at least one pharmaceutically acceptable carrier.

According to one embodiment, a pharmaceutical formulation or a cell culture composition is provided comprising a macrocyclic lactone, combined with at least one co-agent useful for promoting cell regeneration, in particular nerve regeneration, and at least one pharmaceutically acceptable carrier or a medium suitable for cell culture.

According to another embodiment of the invention, the compounds according to the invention and pharmaceutical formulations thereof can be administered after surgery where solid tumors have been removed as a prophylaxis against relapsing and/or metastases.

Methods According to the Invention

According to another aspect, the invention provides a method of preventing, treating or ameliorating a colorectal cancer.

According to another aspect, the invention provides a method of modulating Wnt signalling, in particular down-regulating Wnt signalling, notably in the treatment of neurodegenerative, bone, cardiovascular and metabolic disorders.

According to another aspect, the invention provides a method of modulating Wnt signalling, in particular down-regulating Wnt signalling, notably in the treatment of a cancer such as a cancer selected from breast cancer, melanoma, head and neck cancer, lung cancer, gastric cancer, mesothelioma, glioblastoma, medulloblastoma and cervical cancer.

According to another aspect, the invention provides a method of regenerating a damaged organ or tissue of a subject, in particular for the treatment of neurodegenerative diseases or spinal cord injuries, for example either through in vivo cell regeneration or through ex vivo cell culture before implantation into a subject.

Typically, for colorectal cancer treatment, the therapeutically effective dose of a macrocyclic lactone according to the invention is from about 30 mg/kg body weight to about 120 mg/kg body weight.

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

Patients

In an embodiment, patients according to the invention are patients suffering from a colorectal cancer.

In a particular embodiment, patients according to the invention are suffering from an adenoma, early stage or primary colorectal cancer.

In another embodiment, subjects according to the invention are subjects at risk of developing colorectal cancer due to genetic history or to environmental factors such as sedentary lifestyle and diet rich in animal fat.

In another particular embodiment, patients according to the invention are suffering from an advanced adenocarcinoma (TNM stage III-IV) or/and a metastatic colorectal cancer, oftentimes located in the liver.

In another particular embodiment, patients according to the invention are suffering from a colorectal cancer at the stage of an early carcinoma or early adenoma, typically stages TNM stage II.

In another particular embodiment, patients according to the invention are suffering from a disease or disorder where modulation of Wnt signalling is needed, such as neurodegenerative disorders such as Alzheimer's disease, Parkinson's disease and schizophrenia, bone disorders such as osteoarthritis, osteoporosis and bone mass loss, cardiovascular disorders such as heart failure, myocardial infarction, cardiac hypertrophy and cardiac remodelling and metabolic disorders such as Type II diabetes (Luo et al., 2007, Lab. Invest., 87, 97-103).

In another particular embodiment, patients according to the invention are suffering from a disease or disorder where modulation of Wnt signalling is needed, such as patients suffering from a disorder or condition associated with aberrant Wnt signaling, such as a cancer disorder or condition selected from breast cancer, melanoma, head and neck cancer, lung cancer, gastric cancer, mesothelioma, glioblastoma, medulloblastoma and cervical cancer.

In another particular embodiment, patients according to the invention are suffering from glioblastoma.

In another particular embodiment, patients according to the invention are suffering from melanoma.

References cited herein are hereby incorporated by reference in their entirety. The present invention is not to be limited in scope by the specific embodiments and drawings described herein, which are intended as single illustrations of individual aspects of the invention, and functionally equivalent methods and components are within the scope of the invention. The examples illustrating the invention are not intended to limit the scope of the invention in any way.

EXAMPLES

General Procedures & Conditions

The following studies are conducted to support the effectiveness of macrocyclic lactones according to the invention in the management of colorectal cancer.

The following abbreviations refer respectively to the definitions below:

BrdU (5-bromo-2'-deoxyuridine), DMEM (Dulbecco's modified Eagle's medium), DMSO (Dimethyl Sulfoxide), HBMS (Human Hydroxymethylbilane Synthase), TBP (Human TATA Binding Protein), TCF4 (Human transcription factor 4).

Example 1

Effects of Macrocyclic Lactones on Proliferation in Human Colon Cancer Cells

In order to test the effects of macrocyclic lactones according to the invention in colorectal cancer, the following assay was carried out:

Human colon adenocarcinoma cell line (LS174T), human primary colon cancer cells (CC14) and primary metastatic cells (mCC11) were treated with Avermectin B1 (MicroSource Discovery systems, CT, USA), 5 µM. Control cells were treated with equivalent concentration of DMSO. 48 h after treatment, the percentage of BrdU incorporation was calculated for cells treated with Avermectin B1 as compared to control cells as follows: the number of BrdU positive cells over total number of cells expressed as percentage compared to control cells treated with DMSO only. Cells were cultivated in standard conditions (37° C., 5% $CO_2$) in DMEM containing 10% Fetal Calf Serum.

Figure 1:
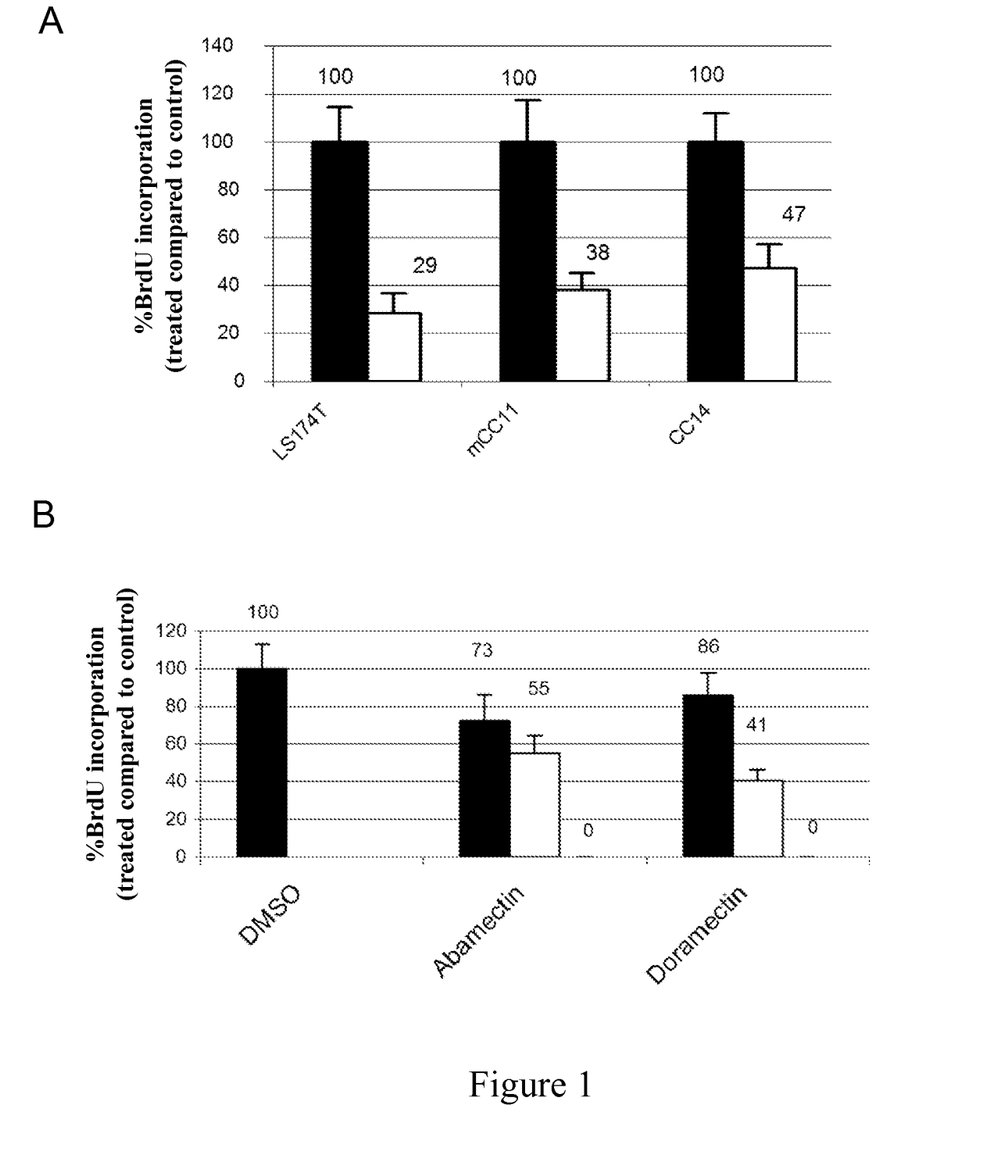
FIGS. 1A-1B shows the effects of macrocyclic lactones according to the invention on proliferation of human colon cancer cells as described in Examples 1 and 3, respectively as measured by BrdU (5-bromo-2'-deoxyuridine) incorporation into human colon cancer cells after 48 hours treatment with a macrocyclic lactone as compared to DMSO control alone. A: Human colon adenocarcinoma (LS174T), primary metastatic (mCC11) cells and human primary colon cancer cells (CC14) treated with Avermectin B1 (MicroSource Discovery systems, CT, USA, 5 µM concentration) (white rectangles) as compared to DMSO (black rectangles); B: Human colon adenocarcinoma cells (LS174T) treated with Abamectin (Sigma #31732) or Doramectin (Sigma #33993) at three different concentrations: 0.1 (black rectangles), 1 (white rectangles) and 5 µM (hatched rectangles).

The data show that Avermectin B1 treatment decreases to a minimum of half the proliferation in each type of cells (FIG. 1A).

Example 2

Specificity of Macrocyclic Lactones on Wnt Pathway

In order to test the specificity of the macrocyclic lactones in the blocking of the Wnt pathway useful in the treatment of human colon carcinomas (Varnat et al., 2010, EMBO Molecular Medicine, 2(11), 440-457), the following assay was carried out:

Key Wnt target gene expression was determined by quantitative real time PCR in LS174 colon adenocarcinoma cell line expressing a dominant negative TCF4 cDNA (dnTCF4) or 12 h after treatment with 5 µM Avermectin B1 (MicroSource Discovery systems, CT, USA). Control cell samples were treated with equivalent concentrations of DMSO. Cells were cultivated in standard conditions as described in Example 1.

Expression levels of individual genes are shown as a percentage compared to their expression levels in control cells treated with DMSO only in the case of Avermectin B1, or transfected with control plasmid in the case of dnTCF4, and are shown in Table 1 below:

TABLE 1

|  | C-MYC | AXIN2 | P21 | LGR5 | EPNB1 | EPHB2 | EPHB3 |
| --- | --- | --- | --- | --- | --- | --- | --- |
| dnTCF4 | 35% | 73% | 2108% | 20% | 571% | 76% | 53% |
| Avermectin B1 | 35% | 62% | 635% | 3% | 277% | 78% | 55% |

These results show that the target gene signature (genes upregulated and genes downregulated) obtained for Avermectin B1 is similar to the profile obtained for dnTCF4 that was used to genetically block the Wnt pathway, indicating specificity of the effects of the macrocyclic lactone according to the invention on this pathway.

Example 3

Dose-Effect of Macrocyclic Lactones on Proliferation in Human Colon Cancer Cells The same assay as described in Example 1 was carried out on human colon adenocarcinoma cell line LS174T where cell samples were either treated with Abamectin (Sigma #31732) or Doramectin (Sigma #33993) at three different concentrations: 0.1, 1 and 5 µM. Control cells were treated with equivalent concentration of DMSO. 48 h after treatment, the percentage of BrdU incorporation was calculated for cells treated with each macrocyclic lactone as compared to control cells as described above. The data show that treatment with both macrocyclic lactones decreases proliferation in a dose-dependent manner (FIG. 1B).

Example 4

Figure 2:
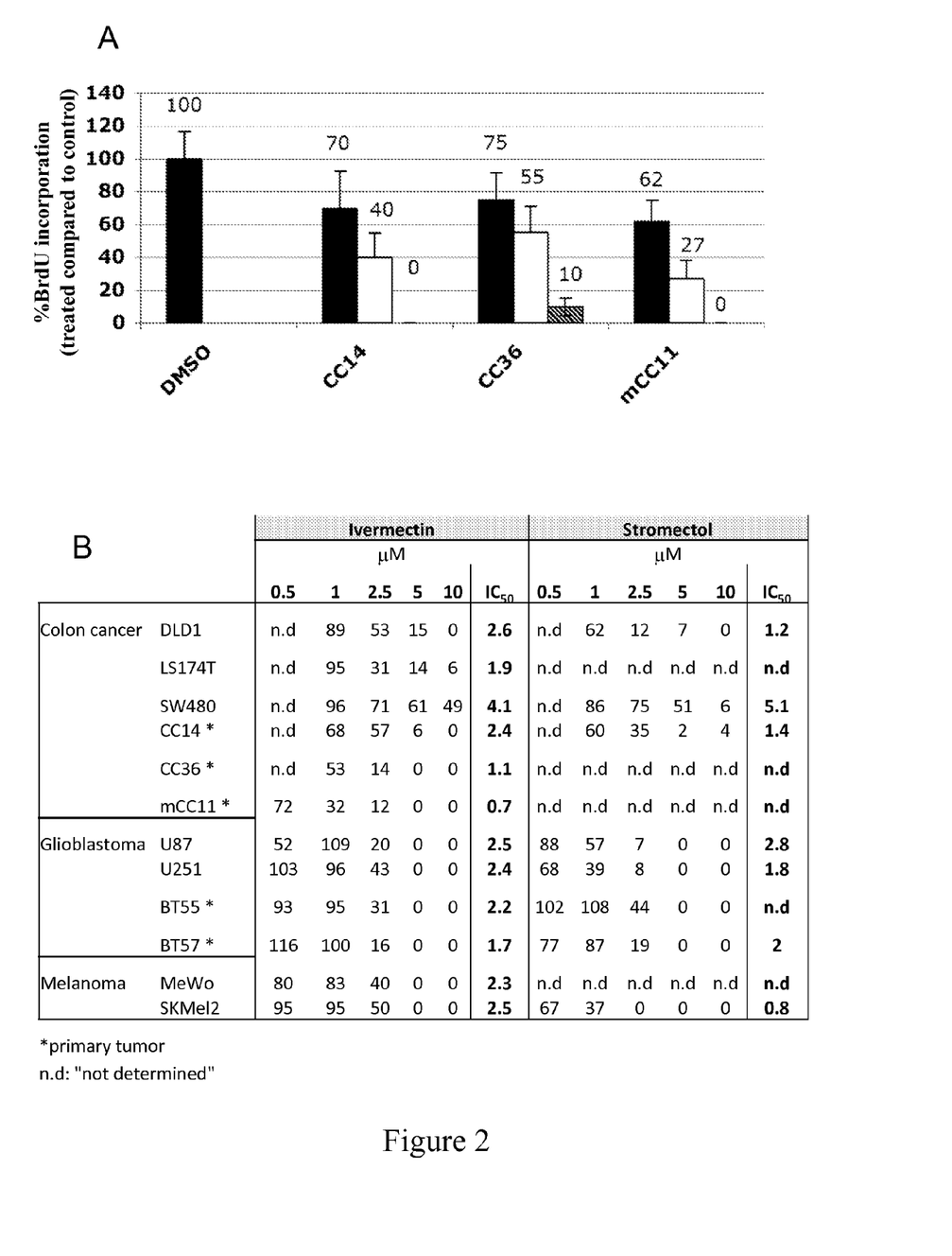
FIGS. 2A-2C show dose effects of macrocyclic lactones on proliferation of colon cancer cells. A: in primary human colon cancer cells as described in Example 4 as measured by BrdU incorporation on human primary colon cancer cells (CC14 (TNMIII) and CC36 (TNMIV)) and primary CC metastatic cells to the liver (mCC11) after 48 hours treatment with Abamectin (Sigma #31732) at three different concentrations: 0.1 (black rectangles), 1 (white rectangles) and 5 µM (hatched rectangles), as compared to DMSO control carrier alone; B: in various cancer cells as described in Example 5 as measured by BrdU incorporation expressed as percentage over carrier treated control and represented by $IC_{50}$ values after 48 hours treatment with different concentrations of Ivermectin and its oral formulation STROMECTOL; C: in various cancer cells as described in Example 5 as measured by BrdU incorporation expressed as percentage over carrier treated control and represented by $IC_{50}$ values after 48 hours treatment with different concentrations of Abamectin, Doramectin and Moxidectin as compared to Ivermectin.

Dose-Effect of Macrocyclic Lactones on Proliferation in Primary Human Colon Cancer Cells The same assay as described in Example 1 was carried out on human primary colon cancer cells (CC14 and CC36) (TNM IV and III, respectively) and primary metastatic cells (mCC11) from the liver of the patient where cell samples were treated with Abamectin (Sigma #31732) at three different concentrations: 0.1, 1 and 5 µM. Control cells were treated with equivalent concentrations of DMSO. 48 h after treatment the level of BrdU incorporation was calculated for cells treated with each macrocyclic lactone as compared to control cells as described above. The data show that treatment with Abamectin decreases proliferation in a dose-dependent manner in those cells (FIG. 2A).

Overall the above data show that macrocyclic lactones are effective Wnt-TCF modulators and are effective in decreasing proliferation on different human primary colon cancer cells.

Example 5

Dose-Effect of Macrocyclic Lactones on Proliferation in Primary Human Colon Cancer Cells The same assay as described in Example 1 was carried out on human primary colon cancer cells (CC14 and CC36) (TNM IV and III, respectively) and primary metastatic cells (mCC11) from the liver of the patient, on the human adenocarcinoma cell lines DLD1, LS174T, and SW180 and on human skin melanoma cell lines MeWo and SKMel2 where cell samples were treated with Ivermectin (Fabron Iberica S.A.U) or Stromectol™ (Merck & Co. Inc.) which is an oral pharmaceutical formulation of semisynthetic Ivermectin (mixture containing at least 90% 5-O-demethyl-22,23-dihydroavermectin $A_{1a}$ and less than 10% 5-O-demethyl-25-de(1-methylpropyl)-22,23-dihydro-25-(1-methylethyl)avermectin $A_{1a}$, generally referred to as 22,23-dihydroavermectin $B_{1a}$ and $B_{1b}$, or $H_2B_{1a}$ and $H_2B_{1b}$) at different concentrations: 0.5, 1, 2.5, 5 and 10 µM (Ivermectin diluted in DMSO, Stromectol in Ethanol). Control cells were treated with equivalent concentrations of DMSO. 48 h after treatment the level of BrdU incorporation was calculated for cells treated with each macrocyclic lactone as compared to control cells as described above. $IC_{50}$ values are calculated by interpolation from a dose response curve fitted using PRISM (Graphpad Software). The data show that treatment with Ivermectin and its oral formulation decreases proliferation in a dose-dependent manner in both human colon cancer cell lines and in cells from primary human colon tumors and also in both human glioblastoma cancer cell lines and in cells from primary human glioblastoma tumors and in skin melanoma cell lines (FIG. 2B).

The same experiment was conducted on human primary colon cancer cells (CC14 and CC36) and primary metastatic cells (mCC11) from the liver of the patient, and LS174T cells where cell samples were treated with Abamectin (Sigma #31732), Doramectin (Sigma #33993) or Moxidectin (Sigma 33746) at different concentrations: 0.5, 1, 2.5, 5 and 10 µM. Results are presented in FIG. 2C in comparison with results with Ivermectin as described above.

Overall the above data show that macrocyclic lactones are effective Wnt-TCF modulators and are effective in decreasing proliferation of different types of cancer cells in vitro represented by glioma, melanoma and colon cancer cells, which supports the beneficial effects of macrocyclic lactones and in particular Ivermectin, Abamectin Doramectin and Moxidectin in the treatment of aberrant Wnt signaling conditions.

Example 6

Effect of Macrocyclic Lactones on Tumor Growth in Mice

The effect of macrocyclic lactones on tumor growth can be determined in vivo in mice according to the following assays:

Mouse Xenografts of Human Colon Cancer (CC) Cells

Six- to eight-week-old female nude NMRI (Naval Medical Research Institute) mice each receive two injections of $10^5$-$10^6$ human DLD1 CC cells on their backs as independent subcutaneous xenografts. As soon as the tumor is palpable (1-2 mm) (usually 7-10 days following xenograft), a range of concentrations of Ivermectin (Fabron Iberica S.A.U) or Abamectin (Sigma #31732) (0 (excipient only), 10, 50 and 100 mg/kg/day) is given by oral gavage combined with corn oil or is administered intra-peritoneally (IP) combined with 2-hydroxypropyl-β-cyclodextrin (Sigma, 45% solution) in a second set of experiments. Tumor size is periodically measured with a caliper. Mice are sacrificed before the tumors approach the legal size limit and the tumors are removed and analysed for proliferation (BrdU assay), apoptosis (Caspase3 assay, Varnat et al., 2009, *EMBO Mol. Med.*, 1, 338-351) and invasion (Varnat et al., 2010, above). Control mice are treated with carrier-only control cells, or cells expressing a dominant-negative TCF4 construct (dnTCF4), which acts to actively repress Wnt-TCF signalling.

Metastasis Assay $10^6$ colon cancer cells expressing β-Galactosidase as a reporter gene (Varnat et al., 2009, above) are injected in the tail vein (i.v.) and mice are given a range of concentrations of Ivermectin (Fabron Iberica S.A.U) or Abamectin (Sigma #31732) (0 (excipient only), 10, 50 and 100 mg/Kg/day) by oral gavage combined with corn oil or administered intra-peritoneally (IP) combined with 2-hydroxypropyl-β-cyclodextrin (Sigma, 45% solution) for 1.5 months starting 2 weeks after injection. Lungs are stained in toto with X-Gal (Stecca et al., 2007, *Proc. Natl. Acad. Sci. USA*, 104, 5895-5900) to reveal metastatic cells and the number of formed metastases is scored for each condition.

Figure 3:
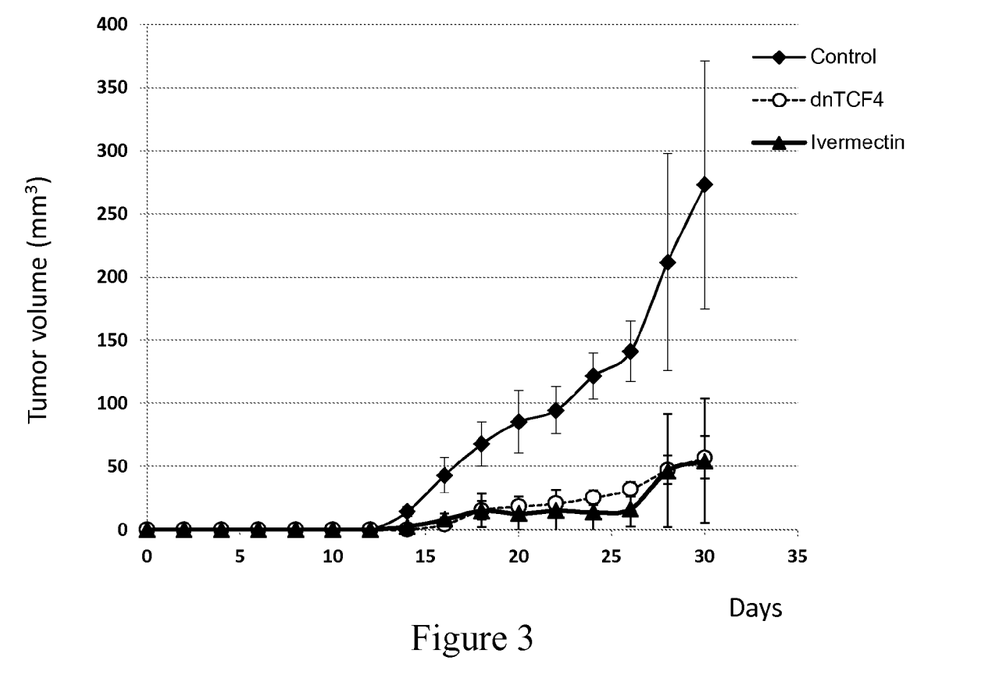
FIG. 3 shows the effects on colon cancer xenograph growth in nude mice of Ivermectin (black triangles) as described in Example 6 as compared to carrier-only control cells (black diamonds), and cells expressing a dominant-negative TCF4 construct (dnTCF4), which acts to actively repress Wnt-TCF signaling (white circles). dnTCF is used as the genetic benchmark for maximum Wnt-TCF inhibition.

Results with human CC cell DLD1 xenografts in nude mice are presented in FIG. 3. These data show that Ivermectin was able to inhibit colon cancer xenograft growth in mice at a concentration of 10 mg/kg to an extent comparable to active transgenic inhibition of Wnt, indicating comparable Wnt inhibition by Ivermectin.

The invention claimed is:

1. A method of down-regulating Wnt signalling in a subject, said method comprising administering in a subject in need thereof an effective amount of macrocyclic lactone or a tautomer, a geometrical isomer, an optically active form, an enantiomeric mixture, a pharmaceutically acceptable salt, a pharmaceutically active derivative thereof or a mixture thereof to down-regulate Wnt signalling.

2. The method according to claim 1, wherein said down-regulation of Wnt signalling treats a disorder selected from a neurodegenerative, a bone, a cardiovascular or a metabolic disorder.

3. The method according to claim 1, wherein said down-regulation of Wnt signalling treats or represses colorectal cancer.

4. The method according to claim 3, wherein said down-regulation of Wnt signalling treats or represses early stage colorectal cancer.

5. The method according to claim 1, wherein said down-regulation of Wnt signalling treats or represses lung cancer.

6. The method according to claim 1, wherein the macrocyclic lactone has Formula (I):

Formula (I)

or is a tautomer, geometrical isomer, optically active form, enantiomeric mixture, pharmaceutically acceptable salt or pharmaceutically active derivative thereof, wherein —X— is selected from the group consisting of —CH=CH—, —CH$_2$—CH(OH)—, —(CH$_2$)$_2$— and —CH$_2$—C(=N—OCH$_3$)—, —Y— is selected from the group consisting of —CH(OH)—, —C(=N—OH)— and —CH(OCH$_3$)—, Z is selected from the group consisting of optionally substituted $C_1$-$C_6$ alkyl, optionally substituted ethyl, optionally substituted $C_2$-$C_6$ alkenyl and optionally substituted $C_3$-$C_8$-cycloalkyl, and W is selected from the group consisting of H and a group of Formula (II):

Formula (II)

wherein $R^1$ is selected from the group consisting of —OH, —NH—C(O)—CH$_3$ and —NH—CH$_3$ and n is an integer selected from 0 and 1.

7. The method according to claim 1, wherein the macrocyclic lactone is selected from ivermectin, abamectin, doramectin, eprinomectin, and selamectin.

8. The method according to claim 1, wherein the macrocyclic lactone is selected from milbemycin oxime and moxidectin.

9. The method according to claim 1, wherein the macrocyclic lactone is an avermectin.

10. The method according to claim 1, wherein the macrocyclic lactone is abamectin.

11. The method according to claim 1, wherein the macrocyclic lactone is avermectin B1a.

12. The method according to claim 1, wherein the macrocyclic lactone is avermectin B1b.

13. The method according to claim 1, wherein the macrocyclic lactone is doramectin.

14. The method according to claim 1, wherein the macrocyclic lactone is ivermectin.

15. The method according to claim 1, wherein the macrocyclic lactone is moxidectin.

16. The method according to claim 1, wherein the macrocyclic is a mixture of macrocyclic lactones.

17. The method according to claim 1, wherein said down-regulation of Wnt signalling treats or represses cancer.

18. The method according to claim 17, wherein the cancer is characterized by cells with up-regulated Wnt signalling.

19. The method according to claim 18, wherein the cancer is selected from the group consisting of breast cancer, melanoma, head and neck cancer, lung cancer, gastric cancer, mesothelioma, glioblastoma, medulloblastoma and cervical cancer.

20. The method according to claim 1, wherein the cancer is a skin cancer.

* * * * *